United States Patent [19]

Klein

[11] Patent Number: 5,111,701

[45] Date of Patent: May 12, 1992

[54] CONTAINER CORNER SECTION GLUE BOND TESTER

[76] Inventor: Gregory N. Klein, 7932 Westview La., Woodridge, Ill. 60517

[21] Appl. No.: 695,395

[22] Filed: May 3, 1991

[51] Int. Cl.⁵ .............................................. G01N 3/08
[52] U.S. Cl. .................................... 73/827; 73/150 A
[58] Field of Search ................... 73/827, 842, 150 A, 73/851

[56] References Cited

U.S. PATENT DOCUMENTS

| | | | |
|---|---|---|---|
| 2,473,517 | 6/1949 | Freedman | 73/827 X |
| 3,396,578 | 8/1968 | Skundberg | 73/827 X |
| 4,862,740 | 9/1989 | Lanier | 73/150 A |
| 4,893,503 | 1/1990 | Kimura et al. | 73/827 X |
| 4,893,513 | 1/1990 | Schroeder et al. | 73/827 |
| 4,934,185 | 6/1990 | Nishiyama et al. | 73/827 X |
| 4,957,004 | 9/1990 | McKinlay et al. | 73/842 |

*Primary Examiner*—Jerry W. Myracle
*Attorney, Agent, or Firm*—Richard W. Carpenter

[57] ABSTRACT

A device for testing the strength of a glue bond of a paperboard container corner section, which section includes one wall panel adhesively secured in face-to-face relationship to a glue flap which is foldably joined to and extends at right angles from another wall panel, by determining the force required to separate the one wall panel from the glue flap.

The device has a pair of platforms mounted for pivotal movement about a common axis, each carrying clamping elements for gripping one portion of a container corner section, and a load cell associated with one platform and operable to measure the force required to separate the one wall panel from the glue flap, based on the relative movement of the platforms.

15 Claims, 3 Drawing Sheets

CONTAINER CORNER SECTION GLUE BOND TESTER

BACKGROUND OF THE INVENTION

1. Field of the Invention

This invention relates to glue bond testers, and more particularly to a device for testing the strength of the glue bond of a paperboard container corner section by pulling one surface away from another surface and calculating the force required to effect the separation of the surfaces.

2. Description of the Background Art

A background art search directed to the subject matter of this invention conducted in the U.S. Patent and Trademark Office disclosed the following U.S. Pat. Nos.:

| | | | |
|---|---|---|---|
| 2,473,517 | 3,396,578 | 3,490,278 | 3,524,345 |
| 4,787,952 | 4,856,325 | 4,862,740 | 4,893,503 |
| 4,893,513 | 4,957,004 | | |

None of the patents uncovered in the search discloses a device that is especially adapted to test a paperboard corner section because it provides means: for gripping separate panels of the corner section with separate clamping mechanisms disposed at right angles to each other, for moving the clamping mechanisms to pull adhered surfaces apart, and for measuring with a load cell the force required to separate the surfaces, based on the movement of the clamping mechanisms relative to each other.

SUMMARY OF THE INVENTION

It is a primary object of the present invention to provide an improved glue bond testing device that is especially designed to test a paperboard container corner section, which section includes one panel adhesively secured to a glue flap that is hinged to an extends at right angles from another panel, by determining the force required to pull the other panel away from the glue flap.

A more specific object of the invention is the provision of a tester of the type described which includes a pair of platforms, mounted for pivotal movement about a common axis and carrying separate clamping means disposed at right angles to each other, one of which is associated with a load cell operable to measure the force required to separate with adhered surfaces, based on the movement of the platform relative to each other.

These and other objects of the invention will be apparent from an examination of the following description and drawings.

It will be understood that, for purposes of clarity, certain elements may have been intentionally omitted from certain views where they are believed to be illustrated to better advantage in other views.

DESCRIPTION OF THE PREFERRED EMBODIMENTS

Figure 1:
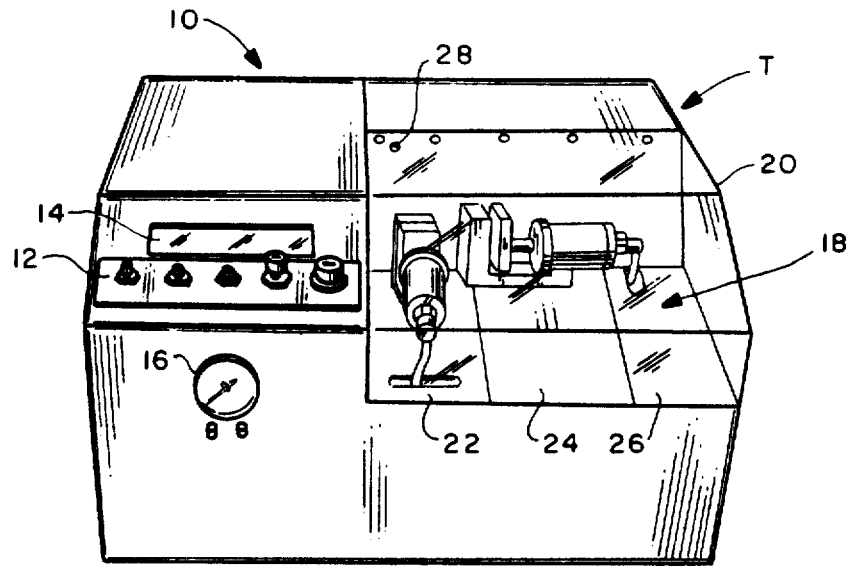
FIG. 1 is a fragmentary isometric view of a testing device embodying features of the present invention.
Figure 3:
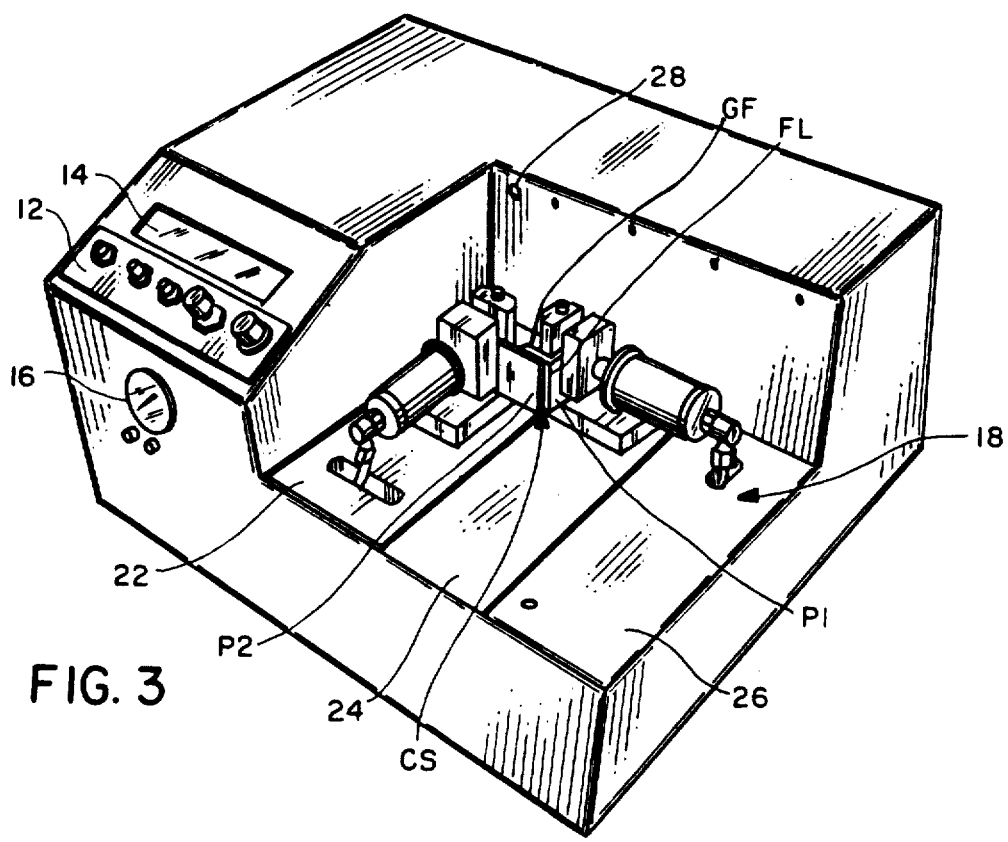
FIGS. 3 and 4 are isometric views of the device illustrated in FIG. 1, but showing the clamping mechanism in different position.
Figure 4:
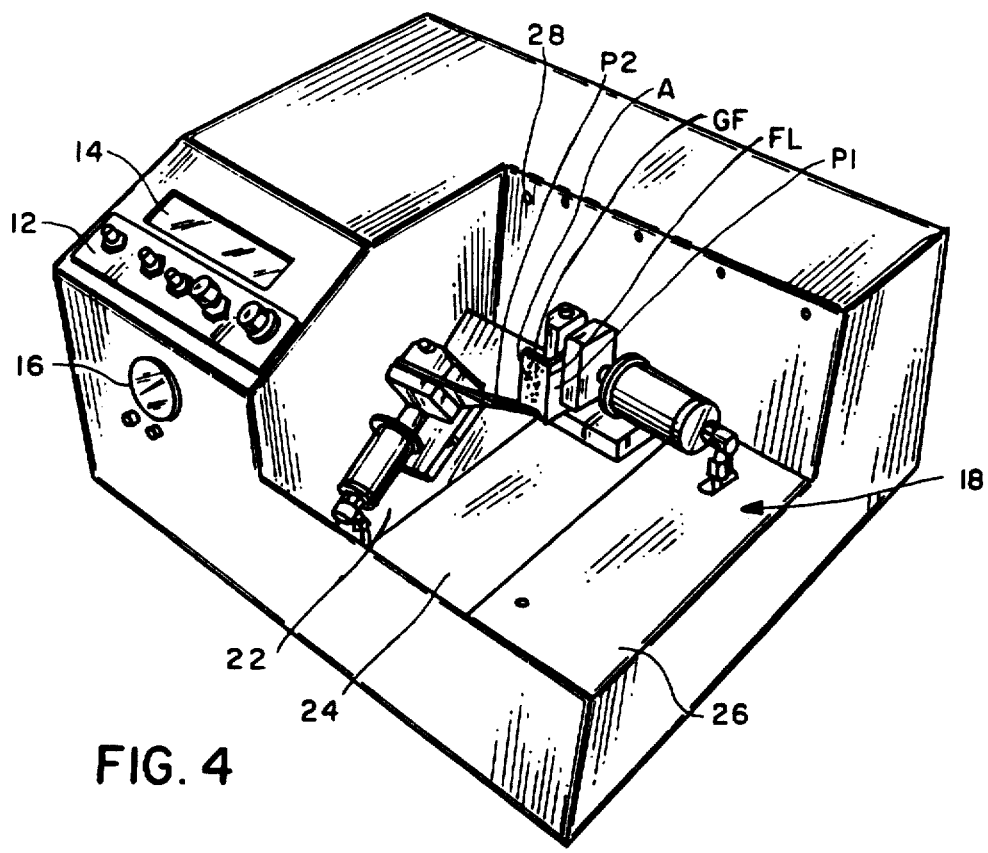

Referring now to the drawings for a better understanding of the invention, it will be seen that the testing device indicated generally at T in FIGS. 1, 3, and 4 is especially designed and adapted to test the glue bond of a corner section CS of a paperboard container.

As best seen in FIGS. 3 and 4, a specimen section of the container corner to be tested, includes portions of a first panel P1, a glue flap GF foldably joined to the first panel on a fold line FL and extending at right angles thereto, and a second panel P2 secured by an adhesive, indicated generally at A, to the glue flap.

Still referring to FIGS. 3 and 4, it will be seen that the testing device T includes a housing, indicated generally at 10, which presents on an upper surface thereof a control/display panel unit 12, having a plurality of switches associated therewith for controlling various operations of the device, and a digital display of the information generated by the testing apparatus.

The housing also contains an external air gauge 16 that indicates the air pressure available for operating the pneumatic cylinders described later in the specification.

At one corner of the housing 10 there is provided a recessed area or work station 18 that can be covered by a hinged lid or cover 20. The work station comprises a horizontal platform or deck which is divided into three separate sections: first and second movable sections 22 and 24, respectively, and a third section 26 that is stationary.

Also, as best seen in FIGS. 3 and 4, there is provided within the work station a clamping mechanism operating switch 28 that is engageable by a portion of the work station cover 20. This is a safety arrangement, as described later in the specification, whereby the clamping means cannot be operated unless the cover 20 is closed and in engagement with switch 18.

Figure 5:
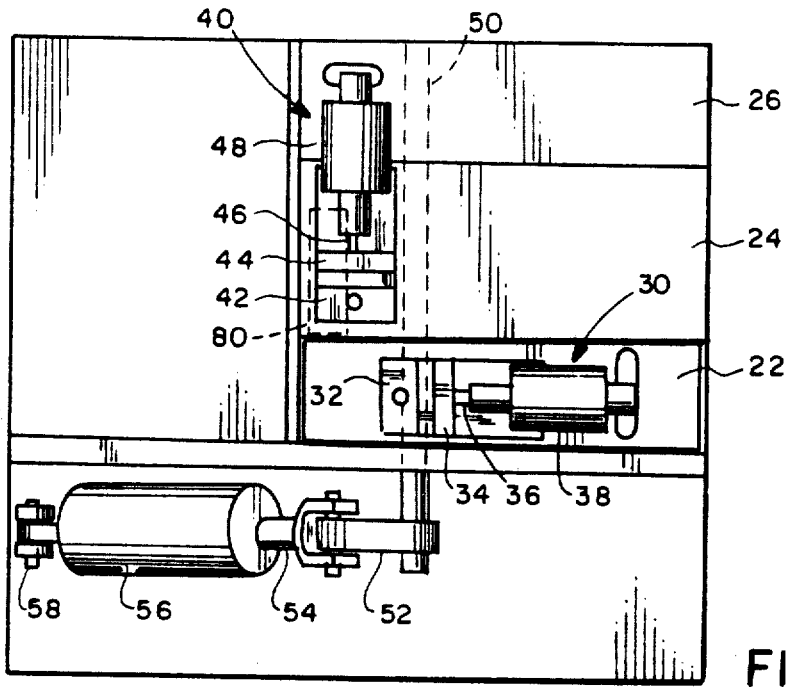
FIG. 5 is a top plan view of the structure illustrated in FIG. 1, with portions of the structure broken away to illustrate some of the structure contained within the housing.
Figure 7:
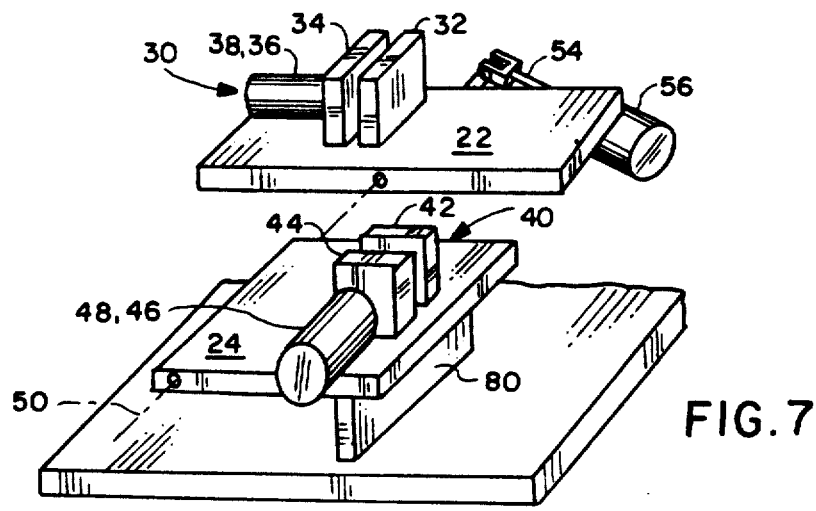
FIG. 7 is an exposed isometric view of portions of the platform and clamping means illustrated in the other views.

As best seen in FIGS. 5 and 7, movable platform sections 22 and 24 are provided with separate first and second clamping assemblies or mechanisms 30 and 40, respectively, that are positioned at right angles to each other.

First clamping assembly 30 includes a fixed jaw 32 and a movable jaw 34, both mounted on platform section 22 with the latter jaw being connected to a piston rod 36 of a pneumatic cylinder 38.

Second clamping assembly 40 also includes a fixed jaw 42 and a movable jaw 44, both mounted on movable platform section 26 with the latter jaw being connected to a piston rod 46 of a pneumatic cylinder 48.

Still referring to FIGS. 5 and 7, it will be seen that each of the movable platform sections 22 and 24 have extending therethrough a horizontally extending drive shaft 50. First movable platform section 22 is secured to the drive shaft for pivotal movement therewith, and second movable platform section 24 is mounted for pivotal movement relative to drive shaft 50.

Figure 6:
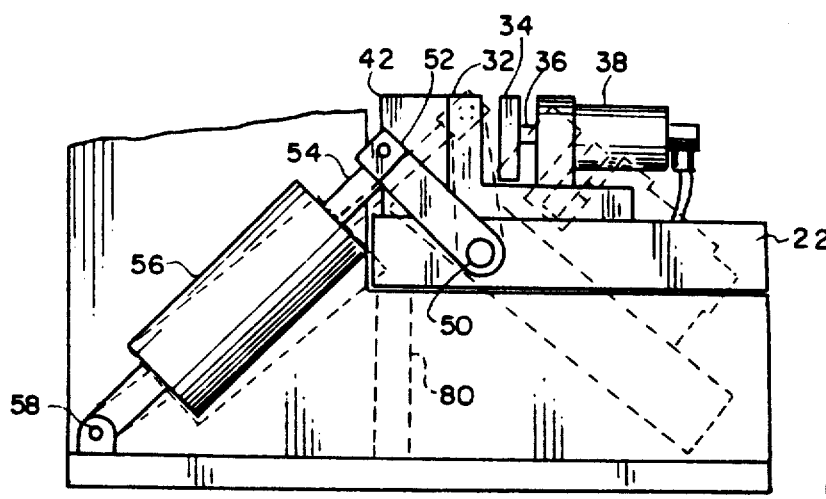
FIG. 6 is a fragmentary side elevation view of the structure illustrated in FIG. 5.

Drive shaft 50 is connected by a link 52 to a piston 54 of a pneumatic cylinder 56 that is mounted within the housing at 58, as best seen in FIGS. 5 and 6.

Figure 2:
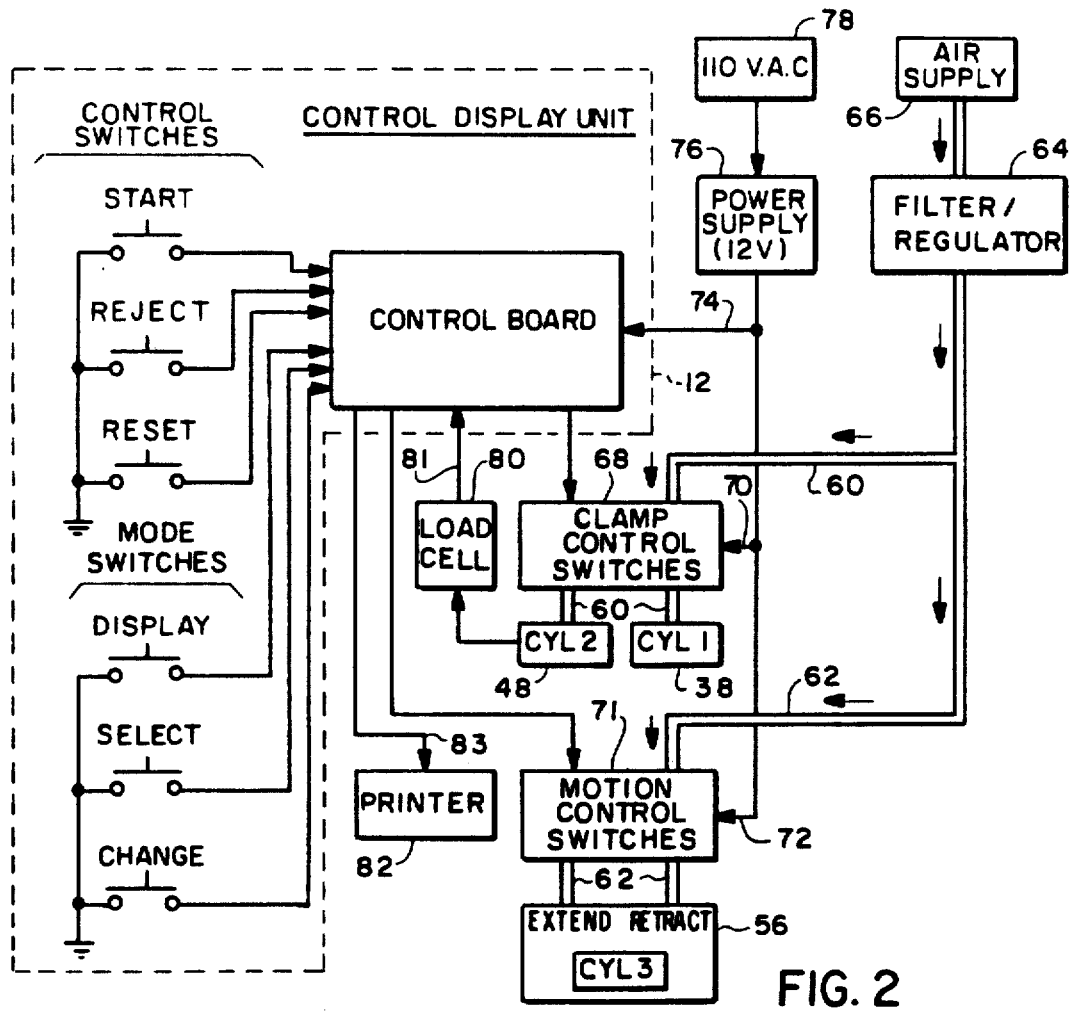
FIG. 2 is a diagrammatic view illustrating the control system for the control and operation of the testing device illustrated in FIG. 1.

All three cylinders are pneumatic and are operated by compressed air from an outside source 66. As best seen in FIG. 2, compressed air is transmitted from the source through a filter/regulator 64 to the clamping cylinders 38 and 48, through a conduit 60, and to motion cylinder 56, through a conduit 62.

Electric power is supplied from a 110 volt power source 78, through a 12 volt transformer 76, to the clamping cylinder switches 68 through a lead 70, to the motion cylinder switches 71 through a lead 72, and to the control/display unit 12 through a lead 74.

As best seen in FIG. 7, a load cell 80 is positioned for contact with movable platform 24 and is connected to the control/display panel unit 12 panel 24 by lead 81.

Additionally, a printer 82 may be connected to the control/display panel unit 12, by lead 83 panel 12 in order to provide a printout of testing information.

After the air supply and electrical power supply have been connected and activated, the device is ready for operation. Cover 20 of the housing can be opened and the specimen of the corner section CS to be tested can be placed in the clamping mechanisms 30 and 40.

Panel P1, which is connected to the glue flap GF, is placed between the jaws of second clamping mechanism 40 on platform section 24, and panel P1, which is adhesively secured to the glue flap GF, is placed between the jaws of first clamping mechanism 30 on platform section 22. Cover 20 is then closed. When the cover engages switch 28, the jaws of each clamping mechanism are automatically brought together to grip and hold the panels of the container corner section to be tested.

A start switch is then closed to actuate motion control cylinder 65 causing drive shaft 50 to rotate and thereby rotate platform section 22. As platform section 22 is rotated about its horizontal axis, clamping assembly 30 moves away from clamping assembly 40 to pull second panel P2 away from glue flap GF, which is hinged to first panel P1, which is in turn held by the jaws of second clamping assembly 40.

As force is applied to pull panel P2 away from glue flap GF, pressure is exerted on second clamping mechanism 40 causing it and related platform section 24 to rotate a very slight amount. The movement of platform section 24 is limited by its engagement with load cell 80, which measures the pressure applied thereagainst, based on the relative movement between first platform section 22 and second platform section 24, to determine the force applied.

The load cell 80 converts the mechanical energy to electrical energy and transmits, to the control/display panel unit via lead 81, electrical signals representative of the force required to separate second panel P2 from glue flap GF, which force indicates the strength of the glue bond at the corner section of the container.

What is claimed is:

1. A device for testing the strength of a glue bond of a paperboard container corner section, which section includes one wall panel adhesively secured in face-to-face relationship to a glue flap which is foldably joined to and extends at right angles from another wall panel, by determining the force required to separate said one wall panel from said glue flap, said device comprising:
   (a) a housing having a control/display unit and an external work station;
   (b) said work station including a platform having:
      (i) a first section mounted on a horizontally disposed drive shaft, for pivotal movement with said drive shaft, and including first clamping means for gripping said one wall panel;
      (ii) a second section mounted on said drive shaft, for limited movement relative to said drive shaft, and including second clamping means disposed at right angles to said first clamping means for gripping said other wall panel;
   (c) means for rotating said drive shaft and said first platform section relative to said second platform section to pull said one wall panel away from said glue flap;
   (d) a load cell associated with said second platform section and being arranged and disposed to measure the force required to separate said one wall panel from said glue flap, based on movement of said second platform section relative to movement of said first platform section, and to transmit to said control/display unit electrical signals representative of said force.

2. A testing device according to claim 1, wherein each of said clamping means includes a fixed jaw mounted on a related movable platform section and a movable jaw mounted for movement toward and away from said fixed jaw by means of a pneumatic piston and cylinder member.

3. A testing device according to claim 2, including a cover member, for covering said clamping means during the operation of said testing device, and a safety control switch, for operating mechanism required to move the movable jaw toward the fixed jaw of each of said clamping means, which switch can only be actuated by contact with said cover when said cover is in a closed position.

4. A testing device according to claim 1, wherein said drive shaft is rotated by a pneumatic piston and cylinder member.

5. A device for testing the strength of a glue bond of a paperboard container corner section, which section includes one wall panel adhesively secured in face-to-face relationship to a glue flap which is foldably joined to and extends at right angles from another wall panel, by determining the force required to separate said one wall panel from said glue flap, said device comprising:
   (a) a control/display unit;
   (b) a first platform section mounted for pivotal movement on a horizontal axis, and including first clamping means for gripping said one wall panel;
   (c) a second platform section mounted for limited movement relative to said axis, and including second clamping means disposed at right angles to said first clamping means for gripping said other wall panel;
   (d) means for rotating said first platform section about said axis relative to said second platform section to pull said one wall panel away from said glue flap;
   (e) a load cell associated with said second platform section and being arranged and disposed to measure the force required to separate said one wall panel from said glue flap, based on movement of said second platform section relative to movement of said first platform section, and to transmit to said control/display unit electrical signals representative of said force.

6. A testing device according to claim 5, wherein said platform sections are mounted on a common drive shaft, said first section being rotatable with said shaft and said second section being rotatable relative to said shaft.

7. A testing device according to claim 6, wherein said drive shaft is rotated by a pneumatic piston and cylinder member.

8. A testing device according to claim 5, wherein each of said clamping means includes a fixed jaw mounted on a related movable platform section and a movable jaw mounted for movement toward and away from said fixed jaw by means of a pneumatic piston and cylinder member.

9. A testing device according to claim 8, including a cover member, for covering said clamping means during the operation of said testing device, and a safety control switch, for operating mechanism required to move the movable jaw toward the fixed jaw of each of said clamping means, which switch can only be actuated by contact with said cover when said cover is in a closed position.

10. A device for testing the strength of a glue bond of a paperboard container corner section, which section includes one wall panel adhesively secured in face-to-face relationship to a glue flap which is foldably joined to and extends at right angles from another wall panel, by determining the force required to separate said one wall panel from said glue flap, said device comprising:
    (a) a control/display unit;
    (b) a first platform section mounted for movement and including first clamping means for gripping said one wall panel;
    (c) a second platform section mounted for movement and including second clamping means disposed at right angles to said first clamping means for gripping said other wall panel;
    (d) means for moving said first platform section relative to said second platform section to pull said one wall panel away from said glue flap;
    (e) a load cell associated with said second platform section and being arranged and disposed to measure the force required to separate said one wall panel from said glue flap, based on movement of said second platform section relative to movement of said first platform section, and to transmit to said control/display unit electrical signals representative of said force.

11. A testing device according to claim 10, wherein said platforms are each mounted for pivotal about a horizontal axis, and including means for rotating said first platform about said horizontal axis.

12. A testing device according to claim 11, wherein said platform sections are mounted on a common drive shaft, said first section being rotatable with said shaft and said second section being rotatable relative to said shaft.

13. A testing device according to claim 12, wherein said drive shaft is rotated by a pneumatic piston and cylinder means.

14. A testing device according to claim 10, wherein each of said clamping means includes a fixed jaw mounted on a related movable platform section and a movable jaw mounted for movement toward and away from said fixed jaw by means of a pneumatic piston and cylinder member.

15. A testing device according to claim 14, including a cover member, for covering said clamping means during the operation of said testing device, and a safety control switch, for operating mechanism required to move the movable jaw toward the fixed jaw of each of said clamping means, which switch can only be actuated by contact with said cover when said cover is in a closed position.

* * * * *